United States Patent
Rueter et al.

(10) Patent No.: US 7,433,736 B2
(45) Date of Patent: Oct. 7, 2008

(54) ATRIAL CAPTURE DETECTION VIA ATRIAL-VENTRICULAR CONDUCTION

(75) Inventors: John C. Rueter, Woodbury, MN (US); Luc R. Mongeon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 630 days.

(21) Appl. No.: 10/284,943

(22) Filed: Oct. 31, 2002

(65) Prior Publication Data

US 2004/0088019 A1    May 6, 2004

(51) Int. Cl.
*A61N 1/08*    (2006.01)

(52) U.S. Cl. .......................... 607/28; 607/25

(58) Field of Classification Search ............... 607/9, 607/27–28, 11, 17, 25
See application file for complete search history.

(56) References Cited

U.S. PATENT DOCUMENTS

| | | | |
|---|---|---|---|
| 5,601,615 A | | 2/1997 | Markowitz et al. |
| 5,741,308 A * | | 4/1998 | Sholder ........................ 607/9 |
| 5,741,312 A * | | 4/1998 | Vonk et al. ................... 607/28 |
| 5,782,889 A * | | 7/1998 | Hognelid et al. ............. 607/28 |
| 5,792,183 A | | 8/1998 | Esler ............................ 607/4 |
| 5,861,012 A * | | 1/1999 | Stroebel ...................... 607/28 |
| 5,902,324 A | | 5/1999 | Thompson et al. ............ 607/9 |
| 5,902,325 A * | | 5/1999 | Condie et al. ................ 607/28 |
| 6,101,416 A * | | 8/2000 | Sloman ....................... 607/28 |
| 6,128,535 A * | | 10/2000 | Maarse ....................... 607/28 |
| 6,477,416 B1 * | | 11/2002 | Florio et al. ................... 607/9 |
| 6,697,673 B1 * | | 2/2004 | Lu ............................... 607/28 |
| 6,788,971 B1 * | | 9/2004 | Sloman et al. ............... 607/28 |
| 6,885,893 B1 * | | 4/2005 | Lu ............................... 607/28 |
| 6,931,281 B2 * | | 8/2005 | Bradley et al. ................. 607/9 |
| 7,027,868 B2 * | | 4/2006 | Rueter et al. ................. 607/28 |
| 2002/0062139 A1 * | | 5/2002 | Ding ........................... 607/25 |
| 2002/0116031 A1 * | | 8/2002 | Vonk ........................... 607/28 |
| 2002/0183798 A1 * | | 12/2002 | Vonk ........................... 607/28 |
| 2003/0125777 A1 * | | 7/2003 | Ding et al. ................... 607/27 |

FOREIGN PATENT DOCUMENTS

EP    1 023 919    8/2000

* cited by examiner

*Primary Examiner*—Kennedy J. Schaetzle
*Assistant Examiner*—Jessica Reidel
(74) *Attorney, Agent, or Firm*—Michael C. Soldner (57) ABSTRACT

Techniques for increasing the accuracy of detection of atrial capture may involve determining a ventricular sensing window for ventricular senses associated with atrial test pulses based on observed ventricular senses. For example, an implanted medical device may deliver atrial test pulses to a patient at a time prior to respective atrial pacing pulses to evaluate atrial capture. The implanted medical device observes ventricular senses in response to the atrial test pulses. The implanted medical device may determine a point such as, for example, a midpoint of the ventricular sensing window for the ventricular senses and shift a midpoint of the default ventricular window to the determined midpoint. Further, the implanted medical device may measure patient parameters, such as heart rate and activity level, and determine a ventricular sensing window for ventricular senses associated with atrial test pulses based on the observed ventricular senses and measured patient parameters.

41 Claims, 6 Drawing Sheets

ATRIAL CAPTURE DETECTION VIA ATRIAL-VENTRICULAR CONDUCTION

TECHNICAL FIELD

The invention relates to cardiac pacing systems and, more particularly, to atrial capture detection and pacing threshold determination.

BACKGROUND

Implanted medical devices, such as pacemakers, may deliver appropriately timed electrical pulses designed to cause the heart to contract or beat, i.e., to "capture" the heart. The stimulation pulses provided by implanted pacemakers usually have well-defined amplitude and pulse width characteristics, which can be adjusted to meet physiologic and device power conservation needs of a particular patient.

The amplitude and pulse width of the pacing pulses must be of an energy magnitude above a stimulation threshold in order to maintain capture of the heart. In order to prolong battery life, however, the energy magnitude of the pacing pulses should not be higher than the stimulation threshold by more than is needed for a reasonable safety margin.

The stimulation thresholds in the atrium and ventricle of a patient often fluctuate in the short term. For example, stimulation thresholds may decrease with exercise and may increase with various other activities, including sleep. Further, stimulation thresholds in the atrium and ventricle may gradually change in the long term. For instance, inflammation in the cardiac tissue around a tip of a pacing lead electrode drives the stimulation threshold up sharply during the first few weeks after implantation of the pacemaker, in turn requiring greater pacing pulse energy to maintain capture. Some of the inflammation reduces over the long-term, causing the stimulation threshold to decrease.

The energy magnitude of the pacing pulses may be determined after implantation and may be adjusted in accordance with the changing stimulation thresholds by performing stimulation threshold tests. Stimulation threshold tests include applying a test pulse and waiting for a cardiac sense in response to the test pulse. A cardiac sense indicates that the test pulse captured the heart and the energy magnitude of the test pulse is above the threshold. Alternatively, failure to detect a cardiac sense indicates that the test pulse did not capture the heart and the energy magnitude of the test pulse is below the threshold. Test pulses are applied until the stimulation threshold, i.e., the point at which a lesser energy pulse results in loss of capture, is found.

SUMMARY

In general, the invention is directed to techniques for determining a ventricular sensing window based on the observed ventricular senses in order to more accurately determine atrial capture via atrial-ventricular conduction during a pacing stimulation threshold test. An implanted medical device, such as a pacemaker, delivers atrial test pulses to a patient at a time prior to respective atrial pacing pulses and observes ventricular senses in response to the atrial test pulses. In accordance with the invention, the implanted medical device determines a ventricular sensing window for the ventricular senses associated with the atrial test pulses based on the observed ventricular senses. The implanted medical device may, for example, determine a midpoint of the ventricular sensing window and shift a midpoint of a default ventricular sensing window to the determined midpoint to more accurately detect whether a corresponding ventricular sense occurs. Alternatively, the implanted medical device may increase the length of a default ventricular sensing window to include the determined midpoint to improve accuracy of detected atrial capture.

Adjusting the ventricular sensing window compensates for an observed delay in ventricular senses that follow atrial test pulses. In particular, when an atrial test pulse is delivered in conjunction with atrial pacing "support" pulses, the ventricular sense in response to the atrial test pulse has been observed to exhibit a noticeable delay, possibly caused by the intrinsic efforts of the heart to maintain a regular rate. Accordingly, adjusting the ventricular sensing window can be effective in compensation for the delay and promoting better synchronization between delivery of the test pulse and activation of the ventricular sensing window.

During a stimulation threshold test, the implanted medical device determines whether a ventricular sense occurs during the adjusted ventricular sensing window. When a ventricular sense does not occur within the adjusted ventricular sensing window, the implanted medical device increases the energy magnitude of the pulse and applies another atrial test pulse. The implanted medical device continues to apply atrial test pulses until a number of atrial test pulses capture the atrium, i.e., result in associated ventricular senses.

The implanted medical device may further adjust the sensing window in response to patient parameters such as heart rate, activity level, and the like. The implanted medical device may store ventricular sensing windows in a memory for use in other stimulation threshold tests.

In one embodiment, the invention provides a method comprising delivering atrial test pulses to a patient at a time prior to respective atrial pacing pulses to evaluate atrial capture, observing ventricular senses in response to the atrial test pulses, and determining a ventricular sensing window for the ventricular senses associated with the atrial test pulses based on the observed ventricular senses.

In another embodiment, the invention provides a device comprising a pacing circuit to generate atrial test pulses, an electrode to deliver the atrial test pulses to a patient prior to respective atrial pacing pulses to evaluate atrial capture, a sensor to detect ventricular senses in response to the atrial test pulses, and a processor to determine a ventricular sensing window for the ventricular senses associated with the atrial test pulses based on the observed ventricular senses.

In another embodiment, the invention provides a method comprising delivering cardiac test pulses to a patient at a time prior to respective cardiac pacing pulses to evaluate capture, observing depolarizations in response to the cardiac test pulses, and determining a sensing window for the depolarizations associated with the cardiac test pulses based on the observed depolarizations.

The invention can provide a number of advantages. In general, the invention is capable of increasing the accuracy of atrial capture detection via atrial-ventricular conduction during a pacing stimulation threshold test. Increasing the accuracy of atrial capture detection may be effective in selecting minimum pacing amplitudes and thereby conserving battery resources. In other words, the invention may prevent selection of pacing amplitudes that are higher than needed for atrial capture. In addition, increasing the accuracy of detecting atrial capture may prevent loss of atrial-ventricular (A-V) synchrony due to application of pulses with an energy magnitude below the stimulation threshold.

The details of one or more embodiments of the invention are set forth in the accompanying drawings and the descrip-

DETAILED DESCRIPTION

Figure 1:
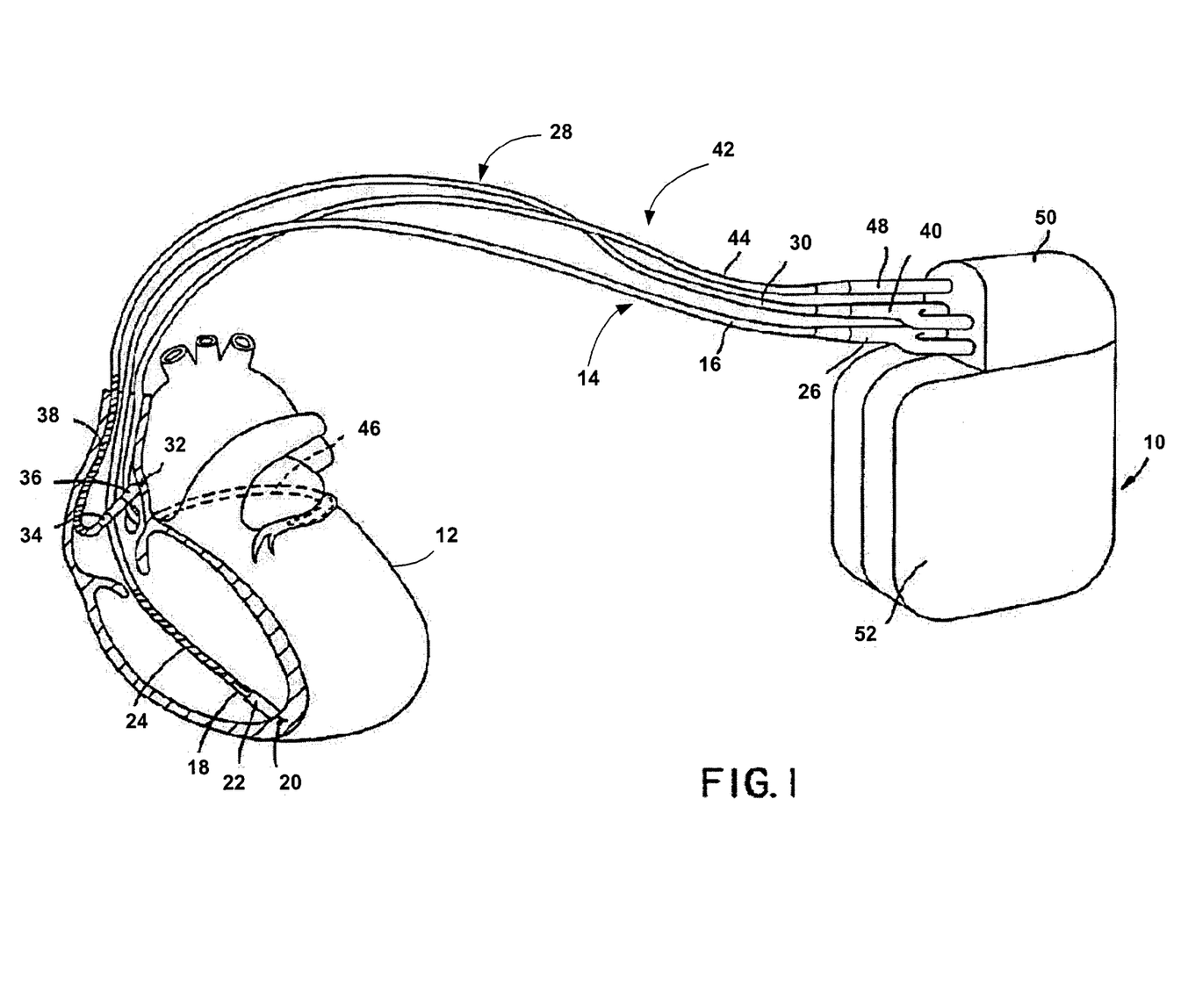
FIG. 1 is a diagram illustrating an implanted medical device useful in delivering cardiac pacing pulses to a heart.

FIG. 1 is a diagram illustrating an implanted medical device 10 useful in delivering cardiac pacing pulses to a heart 12. Device 10, shown in conjunction with heart 12, may be configured to deliver cardiac pacing as well as therapy, such as defibrillation shocks, and monitor the effect of the delivered atrial pacing and therapy. As will be described, implanted medical device 10 can be configured to carry out atrial capture verification via atrial-ventricular conduction. Implanted medical device 10, in accordance with the invention, may be configured to adjust a ventricular sensing window in order to more accurately determine atrial capture during a pacing stimulation threshold test. The ventricular sensing window is a time interval during which implanted medical device 10 waits for detection of a ventricular sense, which, if present, indicates a preceding atrial test pulse captured an atrium of the heart. The specific structure of device 10 is described below for purposes of example, and should not be considered limiting of the invention as broadly embodied herein. For example, the invention may be practiced in a wide variety of device implementations, including devices that provide single chamber pacing and dual chamber pacing. In addition, the invention may be practiced in devices that provide pacing, cardioversion, defibrillation, or any combination thereof.

As shown in FIG. 1, device 10 may include a ventricular lead 14 having an elongated insulative lead body 16, carrying three concentric coiled conductors, separated from one another by tubular insulative sheaths. Located adjacent the distal end of ventricular lead 14 are a ring electrode 18, an extendable helix electrode 20, mounted retractably within an insulative electrode head 22 and an elongated coil electrode 24. Each of electrodes 18, 20, 22, and 24 is coupled to one of the coiled conductors within lead body 16. Electrodes 18, 20, 22, and 24 can be used for both cardiac pacing and sensing of ventricular depolarizations, often referred to as ventricular events. At the proximal end of ventricular lead 14 is a bifurcated connector 26 that carries three electrical connectors, each coupled to one of the coiled conductors.

An atrial lead 28 includes an elongated insulative lead body 30, carrying three concentric coiled conductors, separated from one another by tubular insulative sheaths. Located adjacent the J-shaped distal end of atrial lead 28 are a ring electrode 32 and an extendable helix electrode 34, mounted retractably within an insulative electrode head 36. Each of electrodes 32, 34, and 36 is coupled to one of the coiled conductors within lead body 30. Electrodes 32, 34, and 36 are employed for atrial pacing and for sensing atrial depolarizations, often referred to as atrial events. An elongated coil electrode 38 is provided proximal to ring electrode 32 and coupled to the third conductor within lead body 30. At the proximal end of lead 28 is a bifurcated connector 40 that carries three electrical connectors, each coupled to one of the coiled conductors.

A coronary sinus lead 42 includes an elongated insulative lead body 44, carrying one coiled conductor coupled to an elongated coiled defibrillation electrode 46. Electrode 46, illustrated in broken outline, is located within the coronary sinus and great vein of the heart. At the proximal end of lead 42 is a connector plug 48 that carries an electrical connector, coupled to the coiled conductor. Leads 14, 28, and 42 are inserted into a connector block 51 associated with device 10. Device 10 has an outer housing 52 that may function as a subcutaneous defibrillation electrode that defibrillates either the atria or ventricles.

Figure 2:
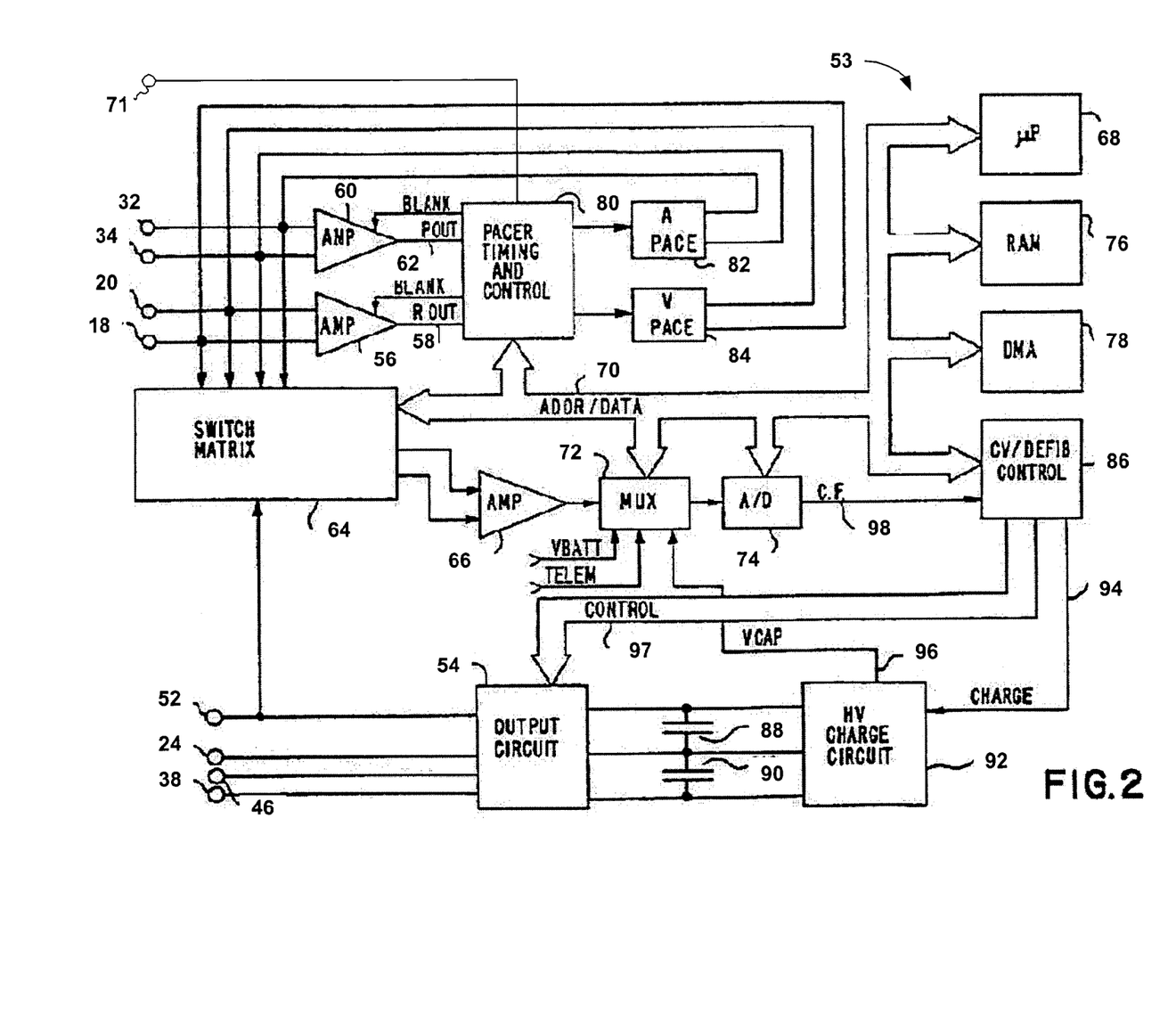
FIG. 2 is a functional schematic diagram illustrating a system capable of delivering cardiac pacing pulses to a heart.

FIG. 2 is a functional schematic diagram illustrating an exemplary system 53 capable of delivering cardiac pacing pulses to a heart of a patient. System 53 may be equipped to detect atrial capture via atrial-ventricular conduction. In accordance with the invention, system 53 may be configured to employ an adjusted ventricular sensing window during an atrial capture test to increase accuracy of detection of atrial capture. As will be described, implanted medical device 10 may observe ventricular senses in response to the atrial test pulses of an energy magnitude known to capture the atrium and determine a ventricular sensing window for the ventricular senses associated with the atrial test pulses based on the observed ventricular senses. The system may be implemented within device 10 of FIG. 1, and may take the form of an implantable device that integrates various pacemaker, cardioverter, and/or defibrillator functions. The diagrams of FIGS. 1 and 2 should be taken as exemplary of the type of device in which the invention may be embodied, however, and not as limiting of the invention as broadly embodied herein.

In the example of FIG. 2, electrode 52 represents the uninsulated portion of a housing of device 10, which may function as a defibrillation electrode. Electrodes 24, 38, 46, and 52 are coupled to high voltage output circuit 54. Electrodes 18 and 20 are coupled to R-wave amplifier 56, which preferably takes the form of an automatic gain controlled amplifier providing an adjustable sensing threshold as a function of the measured R-wave amplitude. A signal is generated on R-out line 58 whenever the signal sensed between electrodes 18 and 20, e.g. a sensed ventricular depolarization, exceeds the present sensing threshold.

Electrodes 32 and 34 are coupled to the P-wave amplifier 60, which also may take the form of an automatic gain controlled amplifier providing an adjustable sensing threshold as a function of the measured P-wave amplitude. A signal is generated on P-out line 62 when the signal sensed between electrodes 32 and 34, e.g. a sensed atrial depolarization, exceeds the sensing threshold. Switch matrix 64 selects which of the available electrodes are coupled to wide band amplifier 66 for use in digital signal analysis. Selection of electrodes is controlled by a controller, which may take the form of a microprocessor 68. Microprocessor 68 controls selection of electrodes by switch matrix 64 via data/address bus 70. Signals from the electrodes selected for coupling to bandpass amplifier 66 are provided to multiplexer 72 and thereafter converted to multi-bit digital signals by A/D converter 74, for storage in memory, such as random access memory (RAM) 76, under control of direct memory access circuit 78.

Microprocessor 68 may employ digital signal analysis techniques to characterize the digitized signals stored in RAM 76 to recognize and classify the heart rhythm using any of a variety of known signal processing methods. In particular, microprocessor 68 may implement a detector that tracks the cycle length and regularity of the heart rhythm. For example, the detector may track atrial events, including atrial test pulses, and ventricular events of the patient to monitor an atrial stimulation threshold test. From the atrial and ventricular events, microprocessor 68 may, for example, determine whether atrial capture occurs during a stimulation threshold test. Further, microprocessor 68 may also determine a ventricular sensing window for the stimulation threshold test by observing ventricular senses in response to atrial test pulses of an energy magnitude known to capture the atrium and store the ventricular sensing window in RAM 76. The remainder of the circuitry illustrated in FIG. 2 is dedicated to the provision of cardiac pacing, cardioversion, and defibrillation therapies.

Pacer timing/control circuitry 80 may include programmable digital counters that control the basic time intervals associated with DDD, VVI, DVI, VDD, AAI, DDI and other modes of single and dual chamber pacing well known to the art. More particularly, circuitry 80 is configured to control escape intervals associated with cardiac pacing in the atrium, ventricle, or both the atrium and ventricle.

Intervals defined by pacing circuitry 80 include atrial and ventricular pacing escape intervals, the refractory periods during which sensed P-waves and R-waves are ineffective to restart timing of the escape intervals, and the pulse widths of the pacing pulses. The durations of these intervals are determined by microprocessor 68, in response to stored data in RAM 76, and are communicated to the pacing circuitry 80 via address/data bus 70. Circuitry 80 also determines the amplitude of the cardiac pacing pulses under control of microprocessor 68. Data stored within RAM 76 may include, for example, stimulation thresholds, ventricular sensing windows determined by observing ventricular senses in response to atrial test pulses of an energy magnitude known to capture the atrium, or any other data collected during a stimulation threshold test or a ventricular sensing window test. Microprocessor 68 may be configured to execute stimulation threshold tests at regular intervals. Further, microprocessor 68 may be configured to execute ventricular sensing window tests, i.e., observing ventricular senses in response to the atrial test pulses of an energy magnitude known to capture the atrium and determining a ventricular sensing window for the ventricular senses associated with the atrial test pulses based on the observed ventricular senses, at regular time intervals. For instance, implanted device 10 may execute ventricular sensing window tests daily, weekly, or monthly. In this manner, the ventricular sensing window and stimulation threshold data stored in RAM 76 may be updated regularly.

During pacing, the escape interval counters within pacer timing/control circuitry 80 are reset upon sensing of R-waves and P-waves, and in accordance with the selected mode of pacing on time-out trigger generation of pacing pulses by pacer output circuits 82 and 84, which are coupled to electrodes 18, 20, 32, and 34. The escape interval counters are also reset upon generation of pacing pulses, and thereby control the basic timing of cardiac pacing functions.

The durations of the intervals defined by the escape interval timers are determined by microprocessor 68 via data/address bus 70. The value of the count present in the escape interval counters when reset by sensed R-waves and P-waves may be used to measure the durations of R-R intervals, P-P intervals, P-R intervals and R-P intervals, also known as V-V intervals, A-A intervals, A-V intervals, and V-A intervals. The A-A interval, for example, is the length of time between a first atrial event and a subsequent atrial event. The resulting measurements can be stored in RAM 76 and used during pacing threshold tests. Further, a sensor 71 may measure a patient parameter such as activity level, heart rate, and the like. Microprocessor may use the measured patient parameters to update durations of the intervals defined by the escape interval timers. Sensor 71 may include sensors such as oxygenation sensors, pressure sensors, pH sensors and respiration sensors, piezoelectric sensors, or any other suitable sensors for providing rate responsive pacing capabilities.

Microprocessor 68 may detect tachycardia via any of a variety of known tachycardia detection algorithms. In response to the detection of atrial or ventricular fibrillation or tachycardia requiring a cardioversion pulse, microprocessor 68 activates cardioversion/defibrillation control circuitry 86, which initiates charging of the high voltage capacitors 88 and 90 via charging circuit 92, under control of high voltage charging control line 94. The voltage on high voltage capacitors 88, 90 is monitored via VCAP line 96, which is passed through multiplexer 72 and in response to reaching a predetermined value set by microprocessor 68, results in generation of a logic signal on Cap Full (CF) line 98, terminating charging. Thereafter, timing of the delivery of the defibrillation or cardioversion pulse is controlled by circuitry 86 via control bus 97. Following delivery of the fibrillation or tachycardia therapy, microprocessor 68 then returns device 10 to cardiac pacing and awaits the next pacing event or sensed atrial or ventricular depolarization.

Figure 3:
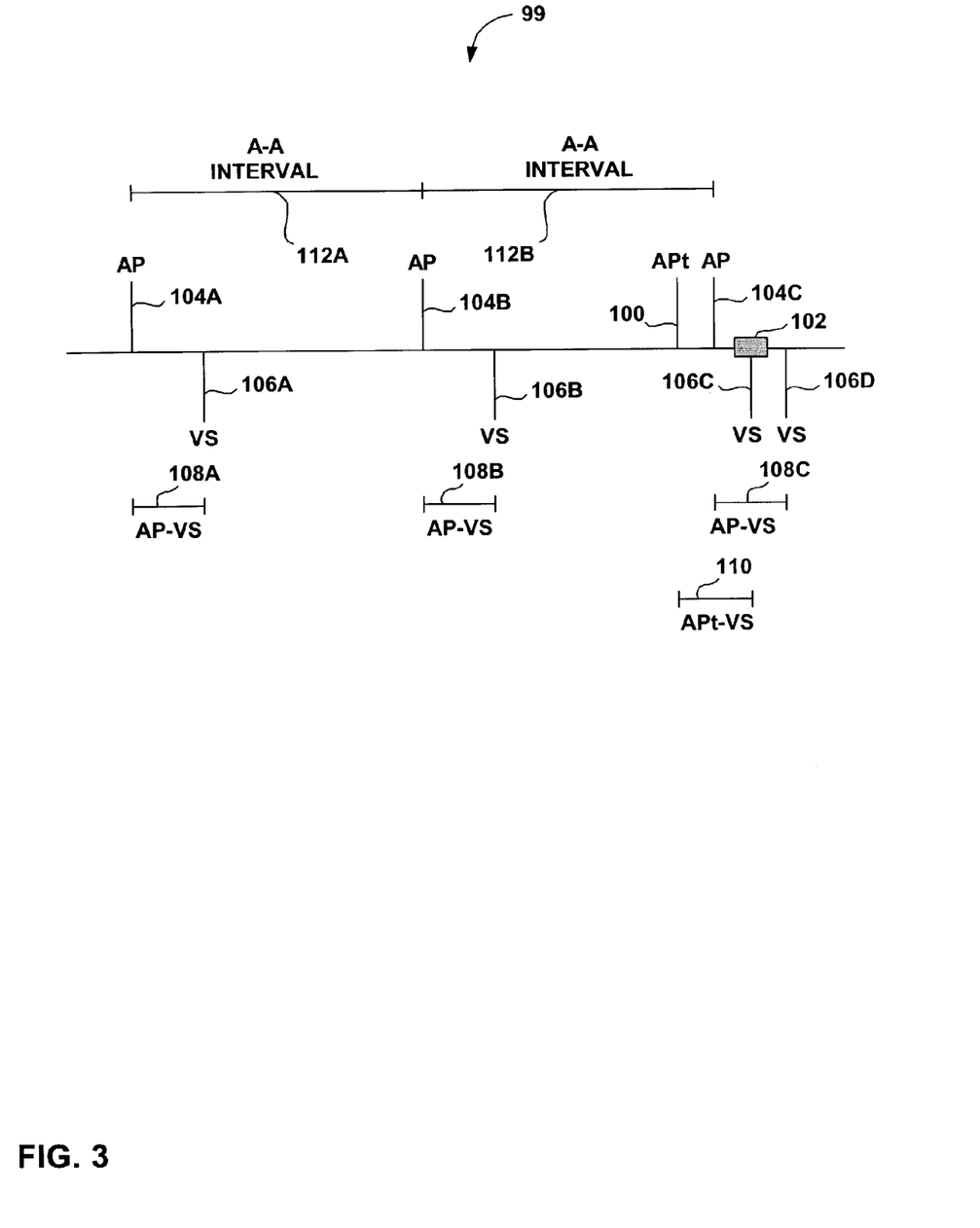
FIG. 3 is a marker channel diagram illustrating an exemplary atrial pacing threshold test in which a ventricular sensing window is adjusted in order to appropriately determine atrial capture.

FIG. 3 is a marker channel diagram illustrating an exemplary atrial pacing stimulation threshold test 99 in which a ventricular sensing window 102, determined during a ventricular sensing window test, is employed to improve accuracy in detection of atrial capture. Atrial pacing stimulation threshold test 99 may be administered on a regular basis to determine stimulation pulse thresholds, such as amplitude and pulse width, necessary for atrial pacing pulses (APs) 104A-104C ("104") to capture the atrium. The stimulation threshold necessary to result in atrial capture may fluctuate in the short term due to various patient activities, and gradually change in the long term due to inflammation and other changes to a heart. Accordingly, ongoing capture detection may be desirable. Although described in terms of atrial pacing stimulation threshold test 99, the techniques of the invention may also readily be applied to ventricular pacing stimulation thresholds.

An implantable medical device, such as implanted medical device 10, tracks atrial pulses 104 and ventricular senses (VSs) 106A-106D ("106"). Following atrial pulses 104, a corresponding ventricular sense 106 occurs, as long as atrial pulses 104 have an energy magnitude that is large enough to capture the atrium. Microprocessor 68 may track the amount of time that occurs between atrial pulses 104 and the corresponding ventricular senses 106, referred to as A-V intervals or atrial pulse-ventricular sense (AP-VS) intervals 108A-108C ("108"), and store AP-VS intervals 108 in RAM 76. AP-VS intervals 108 may differ from patient to patient. Further, AP-VS intervals 108 may vary according to patient parameters, such as physical activity.

Implanted medical device 10 may apply an atrial test pulse 100 at a time interval slightly shorter than atrial pacing escape interval, i.e., slightly shorter than A-A intervals 112. Implanted medical device 10 waits for an associated ventricular sense 106 to occur within ventricular sensing window 102. When an associated ventricular sense 106 occurs within ventricular sensing window 102, which indicates atrial capture, the pulse width and amplitude of an atrial test pulse 100 associated with window 102 exceeds the stimulation threshold. In order to prolong battery life, implanted medical device 10 applies atrial test pulses 100 until a stimulation threshold is detected. The energy magnitude, which includes the pulse width and the amplitude, of the atrial paces 104 are adjusted to be above the detected stimulation threshold by a safety margin.

Implanted medical device 10 determines ventricular sensing window 102 during a ventricular sensing window test based on observed ventricular senses in response to atrial test pulses of an energy magnitude known to capture the atrium. An "expected" midpoint of a ventricular sensing window occurs at a point approximately one of AP-VS interval 108 from the applied test pulse 100, which is the distance that ventricular senses 106 occur following atrial pacing pulses 104. Implanted medical device 10 may, for example, adjust the expected midpoint of a default ventricular sensing window to improve detection of atrial capture. Implanted medical device 10 may, for example shift the midpoint of the default ventricular sensing window to a determined midpoint. Alternatively, implanted medical device may increase the length of the default ventricular sensing window to include a determined midpoint.

The length of time between atrial test pace 100 and ventricular sense 106C is referred to as atrial test pace-ventricular sense (APt-VS) interval 110. APt-VS interval 110 may differ based on the physiology of the heart of the patient. In addition, other patient parameters such as activity level and heart rate may cause APt-VS interval 110 to differ. Implanted medical device may measure these patient parameters and determine ventricular sensing window 102 for ventricular senses 106 associated with atrial test pulses 100 based on the observed ventricular senses 106 and the sensed patient parameter. Ventricular sensing window data may be stored in RAM 76 and implanted medical device 10 may retrieve the corresponding ventricular sensing window data from RAM 76 during stimulation threshold tests. Ventricular sensing window data may include, for example, a midpoint of ventricular sensing window 102, a length of ventricular sensing window 102, or the like. Further, ventricular sensing window data may be updated at a regular interval or when AP-VS intervals 108 increase or decrease by a significant amount.

Figure 4:
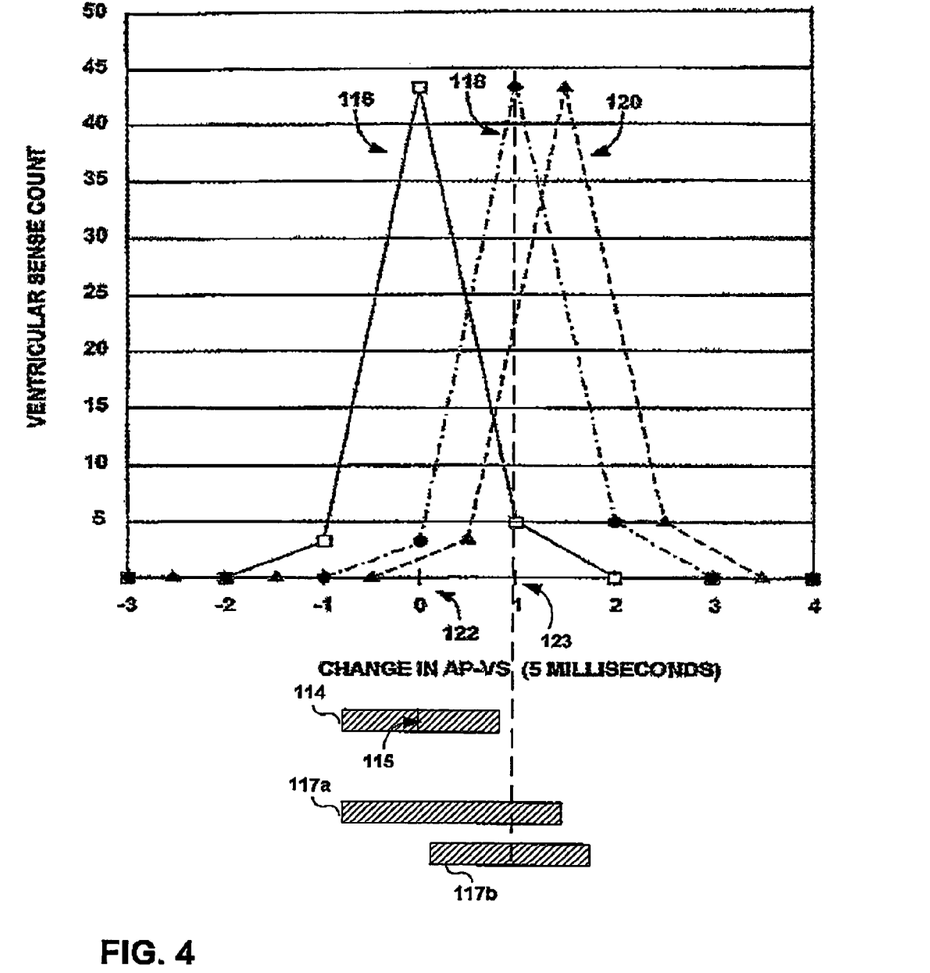
FIG. 4 is a graph illustrating the change in atrial test pulse-ventricular sense (APt-VS) intervals as a function of the amount of time an atrial test pulse is delivered prior to a scheduled atrial pacing pulse.

FIG. 4 is a graph illustrating a shift in ventricular sensing window 102 as a function of the amount of time between an atrial test pulse 100 and a successive atrial pacing pulse 104. The data of the graph is exemplary of ventricular sense data gathered during a study of a patient. The graphs of FIG. 4 illustrate the effect that human physiology of a patient has on the time at which a ventricular sense 106 occurs in response to a test pulse 100. The graph represents the number of ventricular senses 106 that occur in response to atrial pulses, either pacing pulses 104 or test pulses 100, and the time at which they occur in comparison with an "expected" point 122, i.e., 0 on the horizontal axis. For example, plot 116 shows that of fifty-one ventricular pulses detected, forty-three of them occurred at expected point 122. On the other hand, plot 118 shows that of the fifty-one ventricular senses, forty-three of them occurred at approximately five milliseconds later than expected point 122.

In the example of FIG. 4, plot 116 shows ventricular senses 106 that follow atrial pacing pulses 104. As shown in plot 116, the majority of ventricular senses 106 occur at an "expected" location 122. Expected location 122 may be, for example, be an AP-VS interval 108 of previous atrial pacing pulses 104.

Plot 118 and 120 show ventricular senses 106 that follow an atrial test pulse 100. In plot 118, atrial test pulse 100 occurs approximately seventy milliseconds before a successive atrial pacing pulse 104. In plot 120, atrial test pulse 100 occurs approximately ninety-five milliseconds before a successive atrial pacing pulse 104.

The time at which ventricular senses 106 occur following an atrial test pulse 100 delivered before a successive atrial pacing pulse 104 are significantly later than expected point 122, i.e., 5-10 milliseconds. Further, as seen by plots 118 and 120, even a change in the amount of time between atrial test pulse 100 and a successive atrial pacing pulse 104 substantially changes the time at which ventricular senses 106 are detected. For instance, when atrial test pulse 100 occurs at seventy milliseconds before the scheduled atrial pacing pulse 104, the ventricular sense occurs approximately five milliseconds later and when the atrial test pulse 100 at ninety-five milliseconds before the scheduled atrial pacing pulse 104. the ventricular sense occurs approximately eight milliseconds later. In this manner, as the amount of time between test pulse 100 and pacing pulse 104 increases, so does the delay before detecting ventricular senses 106.

As shown in FIG. 3, implanted medical device 10 determines a ventricular sensing window 102 based on observed ventricular senses 106 in response to atrial test pulses 100 of an energy magnitude known to capture the atrium. For instance, a midpoint of ventricular sensing window 102 may shift from a location at approximately an AP-VS interval 108 from atrial test pulse 100 to approximately an AP-VS interval 108 plus five milliseconds from atrial test pulse 100 for the scenario depicted in plot 118.

FIG. 4 illustrates two methods for shifting the midpoint of the ventricular sensing window based on observed ventricular senses in response to atrial test pulses. With regard to plot 118, a midpoint 123 is determined based on observing the ventricular senses in response to atrial test pulses delivered 70 ms prior to atrial pacing pulses. Midpoint 123 may be determined based on an average of measured AP-VS intervals. The default sensing window 114, normally used for observing ventricular senses following atrial pacing pulses, has a midpoint 115 aligned with the "expected" midpoint 122, corresponding to an AP-VS interval. Default sensing window 114 is seen to be terminated prior to the determined midpoint 123 corresponding to a AP-VS interval. Using default sensing window 114 for sensing for a ventricular depolarization following the atrial test pulse delivered approximately seventy ms prior to an atrial pacing pulse would likely result in a LOC detection since default sensing window 114 does not include determined midpoint 123.

A ventricular sensing window 117a for sensing a ventricular depolarization in response to an atrial test pulse is determined based on observed ventricular senses in response to atrial test pulses. Ventricular sensing window 117a is determined by increasing the length of default sensing window 114 to include determined midpoint 123. Alternatively, a ventricular sensing window 117b based on observed ventricular senses in response to atrial test pulses is determined by shifting default sensing window midpoint 115 to the determined midpoint 123. Determined ventricular sensing window 117b is defined by the same time interval duration as default sensing window 114 but is centered on the determined midpoint 123.

Figure 5:
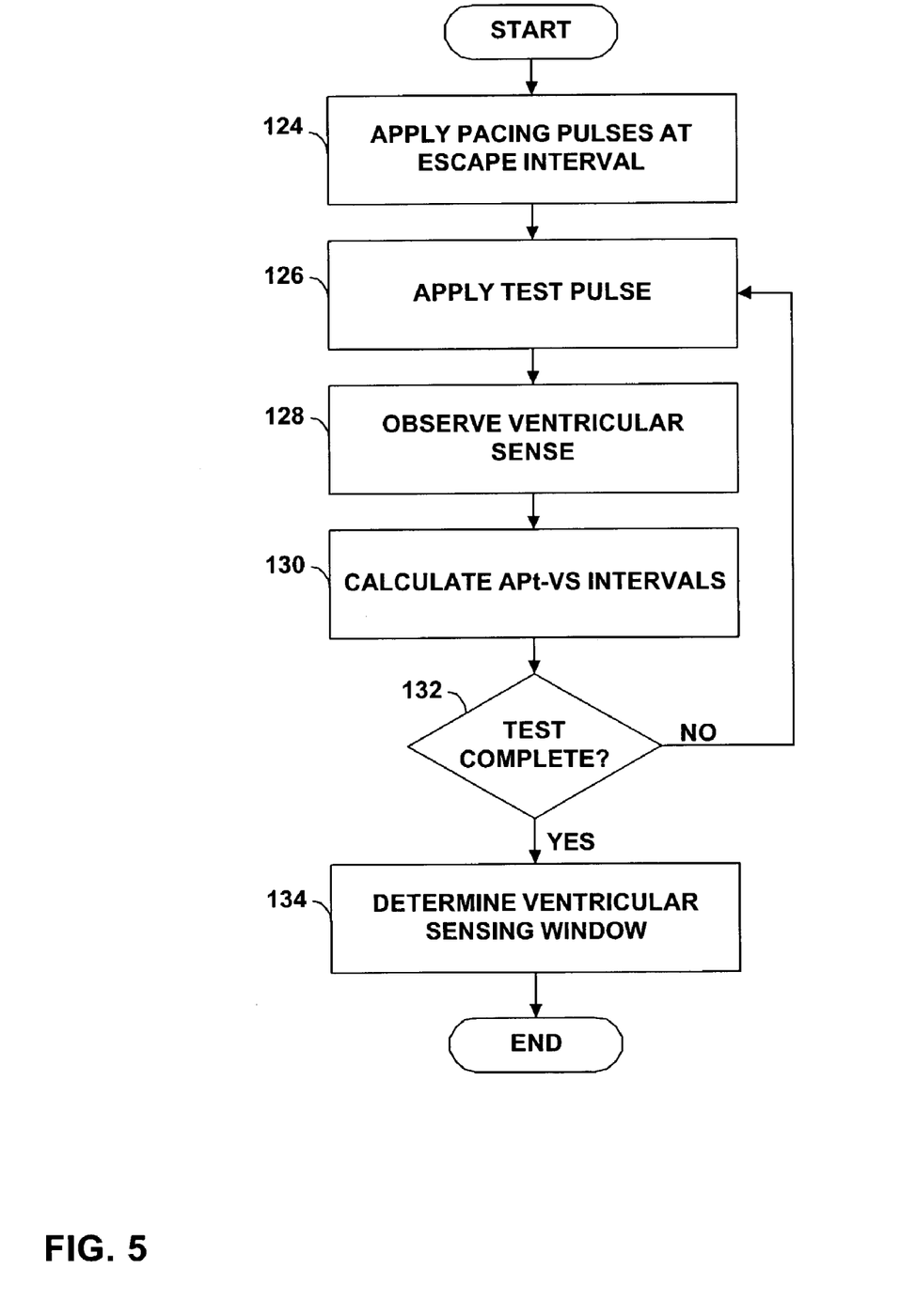
FIG. 5 is a flow diagram illustrating a technique for determining a ventricular sensing window based on observed ventricular senses associated with atrial test pulses.

FIG. 5 is a flow diagram illustrating a technique for determining a ventricular sensing window 102 based on observed ventricular senses 106 associated with atrial test pulses 100. Implanted medical device 10 may apply atrial pacing pulses 104 according to a fixed atrial pacing escape interval, i.e., A-A interval 112 (124). Implanted medical device 10 applies an atrial test pulse 100 of an energy magnitude sufficient to capture the atrium at a time prior to a scheduled atrial pacing pulse 104 (126). For instance, implanted medical device 10 may apply atrial test pulse 100 at about seventy milliseconds prior to the scheduled atrial pacing pulse 104. The time at which implanted medical device 10 applies atrial test pulse 104 may range, for example, between fifty and one hundred milliseconds prior to a atrial pacing pulse 104 as programmed by a physician.

Implanted medical device observes a ventricular sense 106 associated with atrial test pulse 100 (128) and calculates an APt-VS interval 110 for the atrial capture (130). APt-VS interval 110 is longer than AP-VS intervals 108 due to the heart attempting to keep a regular ventricular rate. For instance, APt-VS interval 110 may occur approximately five milliseconds later than would AP-VS interval 108.

Implanted medical device determines whether the ventricular sensing window test is complete (132). The ventricular sensing window test may be complete upon calculating a threshold number of ventricular sensing windows for the atrial test pulse 100 applied prior to a scheduled atrial pacing pulse 104. The amount of time between atrial test pulse 100 and the scheduled atrial pacing pulse 104 remains the same during the ventricular sensing window test. When the ventricular sensing window test is not complete, implanted medical device 10 applies another atrial test pulse 100.

When the ventricular sensing window test is complete, implanted medical device 10 determines a ventricular sensing window (134). For example, implanted medical device 10 may determine an average APt-VS interval 110 length from the calculated APt-VS intervals 110 and determine a midpoint of a ventricular sensing window 102 to occur at the average APt-VS interval 110 length. Implanted medical device 10 may, for example shift the midpoint of a default ventricular sensing window to the determined midpoint. Alternatively, implanted medical device may increase the length of a default ventricular sensing window to include the determined midpoint.

Figure 6:
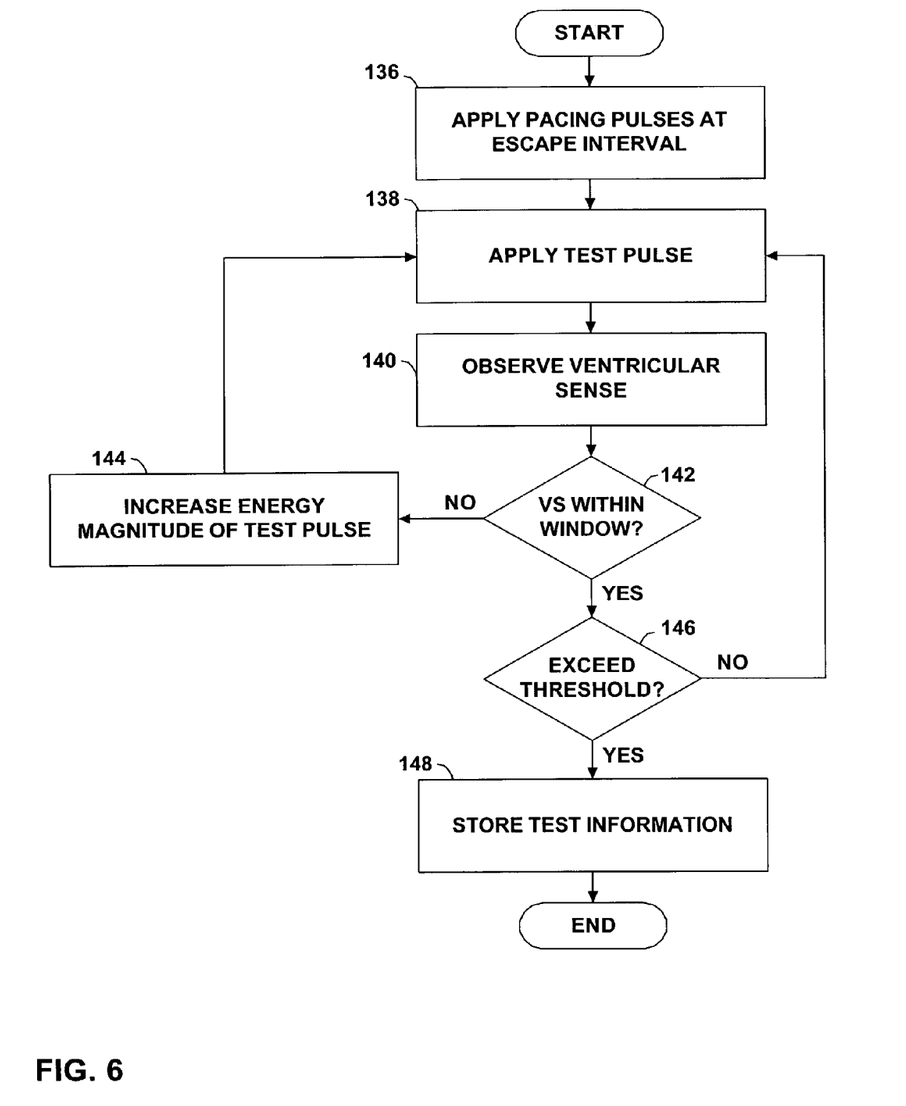
FIG. 6 is a flow diagram illustrating a technique for administering a stimulation threshold test using a ventricular sensing window determined based on observed ventricular senses associated with atrial test pulses.

FIG. 6 is a flow diagram illustrating a technique for administering a stimulation threshold test using a ventricular sensing window 102 determined based on observed ventricular senses 106 associated with atrial test pulses 100. Implanted medical device 10 may apply atrial pacing pulses 104 according to a fixed atrial pacing escape interval, i.e., A-A interval 112 (136). Implanted medical device 10 applies an atrial test pulse 100 at a time prior to a scheduled atrial pacing pulse 104 (138). Implanted medical device 10 may begin a stimulation threshold test by applying a lower energy test pulse and successively moving up to higher energy test pulses until capture is achieved in order to prolong battery life.

Implanted medical device 10 observes a ventricular sense 106(140) and determines whether ventricular sense 106 occurred within the ventricular sensing window 102 (142). Ventricular sensing window 102 may be determined during the ventricular window test. When a ventricular sense 106 is not detected within ventricular sensing window 102, implanted medical device 10 increases an energy magnitude associated with atrial test pulse 100 (144) and applies a subsequent atrial test pulse 100 at a atrial test pulse escape interval. For example, implanted medical device may increase an amplitude of test pulse 100, a pulse width of test pulse 100, a combination of amplitude and pulse width, or other characteristic of test pulse 100.

When a ventricular sense 106 is detected within ventricular sensing window 102, implanted medical device 10 determines whether a number of ventricular senses 106, associated with an atrial test pulse 100 and having similar energy magnitudes, detected within ventricular sensing window 102 exceeds a threshold (146). When the number of ventricular senses 106 detected within ventricular sensing window 102 exceeds a threshold, implanted medical device 10 stores atrial stimulation threshold test information (148). For example, implanted medical device 10 may store atrial stimulation threshold test information when two out of the last three ventricular senses 106 associated with atrial test pulses 100 of similar energy magnitude are detected within ventricular sensing window 102. Alternatively, a number of successive ventricular senses 106 may need to be detected within ventricular sensing window 102 in order to store atrial test information. For instance, implanted medical device 10 may store atrial test information when three consecutive ventricular senses 106 associated with atrial test pulses 100 of similar energy magnitude are detected within ventricular sensing window 102.

Atrial stimulation threshold test information may include, for example, amplitude and pulse width of atrial test pulse 100, the amount of time between atrial test pulse 100 and the successive atrial pacing pulse 104, and patient parameters such as activity level and heart rate at the time at which the stimulation threshold test was conducted. Atrial test information may be stored as a table, a tree, a link list, a database, or any other type of data structure.

Various embodiments of the invention have been described. These and other embodiments are within the scope of the following claims.

What is claimed is:

1. A method comprising:
    delivering an atrial pacing pulse and a next atrial pacing pulse to a patient, the atrial pacing pulse and the next atrial pacing pulse being separated by an atrial escape interval;
    tracking ventricular senses following the atrial pacing pulse and the next atrial pacing pulse;
    determining an expected midpoint of a ventricular sensing window corresponding to a time of a tracked ventricular sense;
    delivering an atrial test pulse during the atrial escape interval following the atrial pacing pulse and at a predetermined time period prior to the next atrial pacing pulse to evaluate atrial capture;
    observing a ventricular sense in response to the atrial test pulse;
    determining a shift in the expected midpoint of the ventricular sensing window in response to the observed ventricular sense, the shift corresponding to a time that occurs between the atrial test pulse and the observed ventricular sense; and
    determining the ventricular sensing window for the ventricular sense associated with the atrial test pulse based on the determined shift of the expected midpoint.

2. The method of claim 1, wherein determining a ventricular sensing window for the ventricular sense associated with the atrial test pulse includes determining a midpoint of the ventricular sensing window for the ventricular sense based on the determined shift of the expected midpoint.

3. The method of claim 2, further comprising shifting a midpoint of a default ventricular sensing window to the determined midpoint, the midpoint of the default ventricular sensing window corresponding to the expected midpoint.

4. The method of claim 2, further comprising increasing the length of a default ventricular sensing window to include the determined midpoint.

5. The method of claim 2, wherein determining a midpoint of the ventricular sensing window includes:
   calculating an atrial test pulse-ventricular sense (APt-VS) interval associated with each of a plurality of atrial test pulses; and
   calculating an average of the APt-VS intervals to determine the midpoint of the ventricular sensing window.

6. The method of claim 1, wherein the atrial test pulse is of an energy magnitude known to capture the atrium.

7. The method of claim 1, further comprising delivering multiple atrial test pulses wherein the atrial test pulses are of a similar energy magnitude.

8. The method of claim 1, further comprising performing an atrial stimulation threshold test using the determined ventricular sensing window.

9. The method of claim 8, wherein performing an atrial stimulation threshold test includes:
   applying an atrial stimulation test pulse; and
   increasing an energy magnitude of the atrial stimulation test pulse when a ventricular sense does not occur within the determined ventricular sensing window.

10. The method of claim 9, wherein increasing the energy magnitude of the atrial stimulation test pulse includes increasing an amplitude of the atrial stimulation test pulse.

11. The method of claim 9, wherein increasing the energy magnitude of the atrial stimulation test pulse includes increasing a pulse width of the atrial stimulation test pulse.

12. The method of claim 1, further comprising storing the determined ventricular sensing window in memory.

13. The method of claim 1, further comprising updating the determined ventricular sensing window.

14. The method of claim 13, wherein updating the determined ventricular sensing window includes updating the determined ventricular sensing window at a regular interval.

15. The method of claim 14, wherein the regular interval includes one of daily, weekly, and monthly.

16. The method of claim 1, further comprising:
   sensing a patient parameter;
   determining the ventricular sensing window for the ventricular sense associated with the atrial test pulse based on the determined shift and the sensed patient parameter.

17. The method of claim 16, wherein the patient parameter includes at least one of an activity level of the patient and a heart rate.

18. An implantable medical device comprising:
   a pacing circuit to generate atrial pacing pulses separated by an atrial escape interval and to generate atrial test pulses;
   an electrode to deliver each of the atrial test pulses to a patient during the atrial escape interval following an atrial pacing pulse and at a predetermined time period prior to a next atrial pacing pulse to evaluate atrial capture;
   a sensor to detect ventricular senses in response to the atrial pacing pulse, the next atrial pacing pulse and the atrial test pulses; and
   a processor configured to control the pacing circuit to generate the atrial pacing pulses separated by the atrial escape interval and to generate the atrial test pulses during the atrial escape interval, determine an expected midpoint of a ventricular sensing window corresponding to a time of a ventricular sense following an atrial placing pulse, determine a shift in the expected midpoint of the ventricular sensing window in response to a time of a ventricular sense following an atrial test pulse, and to determine a ventricular sensing window for the ventricular senses associated with the atrial test pulses based on the determined shift.

19. The device of claim 18, wherein the processor determines a ventricular sensing window for the ventricular senses associated with the atrial test pulses by determining a midpoint of the ventricular sensing window for the ventricular senses based on the determined shift.

20. The device of claim 19, wherein the processor shifts a midpoint of a default ventricular sensing window to the determined midpoint, the midpoint of the default ventricular sensing window corresponding to the expected midpoint.

21. The device of claim 19, wherein the processor increases the length of a default ventricular sensing window to include the determined midpoint.

22. The device of claim 19, wherein the processor determines the midpoint of the ventricular sensing window by calculating an atrial test pulse-ventricular sense (APt-VS) interval associated with each of the atrial test pulses and calculating an average of the APt-VS intervals to determine the midpoint of the ventricular sensing window.

23. The device of claim 18, wherein the device performs an atrial stimulation threshold test using the determined ventricular sensing window.

24. The device of claim 18, wherein the processor stores the determined ventricular sensing window in memory.

25. The device of claim 24, wherein the memory is random access memory.

26. The device of claim 18, wherein the processor updates the determined ventricular sensing window.

27. The device of claim 18, further comprising a sensor to sense a patient parameter, and wherein the processor determines the ventricular sensing window for the ventricular senses associated with the atrial test pulses based on the determined shift and the sensed patient parameter.

28. The device of claim 27, wherein the patient parameter includes at least one of an activity level of the patient and a heart rate.

29. The device of claim 27, wherein the sensor includes at least one of an oxygenation sensor, a pressure sensor, a pH sensor, a respiration sensor, and a piezoelectric sensor.

30. A method comprising:
   delivering a cardiac pacing pulse and a next cardiac pacing pulse to a patient, the cardiac pacing pulse and the next cardiac pacing pulse being separated by an escape interval;
   tracking senses following the cardiac pacing pulse and the next cardiac pacing pulse;
   determining an expected midpoint of a sensing window corresponding to a time of a tracked sense;
   delivering a cardiac test pulse during the escape interval following the cardiac pacing pulse and at a predetermined time period prior to the next cardiac pacing pulse to evaluate capture;
   observing a depolarization in response to the cardiac test pulse;
   determining a shift in the expected midpoint of the sensing window in response to the observed depolarization, the shift corresponding to a time that occurs between the cardiac test pulse and the observed depolarization; and
   determining a sensing window for the depolarization associated with the cardiac test pulse based on the determined shift.

31. The method of claim 30, wherein the cardiac test pulse includes an atrial test pulse.

32. The method of claim 30, wherein the cardiac test pulse includes a ventricular test pulse.

33. An implantable medical device comprising:
a pacing circuit to generate cardiac pacing pulses separated by an escape interval and to generate cardiac test pulses;
an electrode to deliver each of the cardiac test pulses to a patient during the escape interval following a cardiac pacing pulse and at a predetermined time period prior to a next cardiac pacing pulse to evaluate capture;
a sensor to detect depolarizations in response to the cardiac pacing pulses and the next cardiac pacing pulses and the cardiac test pulses; and
a processor configured to control the pacing circuit to generate the cardiac pacing pulses separated by the escape interval and to generate the cardiac test pulses during the escape interval, determine an expected midpoint of a sensing window corresponding to a time of a depolarization following a cardiac pacing pulse, determine a shift in the expected midpoint of the sensing window in response to a time of a depolarization following a cardiac test pulse, and to determine a sensing window for the depolarizations associated with the cardiac test pulses based on the determined shift.

34. The device of claim 33, wherein the cardiac test pulses include atrial test pulses.

35. The device of claim 33, wherein the cardiac test pulses include ventricular test pulses.

36. An implantable medical device comprising:
means for delivering an atrial pacing pulse and a next atrial pacing pulse, the atrial pacing pulse and the next atrial pacing pulse being separated by an atrial escape interval;
means for tracking ventricular senses following the atrial pacing pulse and the next atrial pacing pulse;
means for determining an expected midpoint of a ventricular sensing window corresponding to a time of a tracked ventricular sense;
means for delivering an atrial test pulse to a patient during the atrial escape interval following the atrial pacing pulse and at a predetermined time period prior to the next atrial pacing pulse to evaluate atrial capture;
means for observing a ventricular sense in response to the atrial test pulse;
means for determining a shift in the expected midpoint of the ventricular sensing window in response to the observed ventricular sense, the shift corresponding to a time that occurs between the atrial test pulse and the observed ventricular sense; and
means for determining a ventricular sensing window for the ventricular sense associated with the atrial test pulse based on the determined shift.

37. The device of claim 36, wherein the determining means determines a midpoint of the ventricular sensing window for the ventricular sense associated with the atrial test pulse based on the determined shift of the expected midpoint.

38. The device of claim 37, further comprising means for shifting a midpoint of a default ventricular sensing window to the determined midpoint, based on the determined shift of the expected midpoint.

39. The device of claim 37, further comprising means for increasing the length of a default ventricular sensing window to include the determined midpoint.

40. The device of claim 37, wherein the determining means includes:
means for calculating an atrial test pulse-ventricular sense (APt-VS) interval associated with each of a plurality of atrial test pulses; and
means for calculating an average of the APt-VS intervals to determine the midpoint of the ventricular sensing window.

41. A method for setting a ventricular sensing window for use during atrial threshold testing, the method comprising:
delivering an atrial pacing pulse and a next atrial pacing pulse to a patient, the atrial pacing pulse and the next atrial pacing pulse being separated by an atrial escape interval;
determining an expected midpoint of a default ventricular sensing window corresponding to an interval between the atrial pacing pulse and a subsequent ventricular sense (AP-VS);
delivering an atrial test pulse during the atrial escape interval following the atrial pacing pulse and at a predetermined time period prior to the next atrial pacing pulse to evaluate atrial capture;
observing a ventricular sense in response to the atrial test pulse;
determining a shift in the expected midpoint of the default ventricular sensing window in response to the observed ventricular sense, the shift corresponding to a time that occurs between the atrial test pulse and the observed ventricular sense; and
determining a ventricular sensing window for the ventricular sense associated with the atrial test pulse based on the determined shift, determining the ventricular sensing window comprising adjusting the default ventricular sensing window in response to the determined shift,
wherein determining the ventricular sensing window further comprises:
delivering a plurality of atrial test pulses each having a similar energy magnitude known to capture the atrium,
calculating an atrial test pulse-ventricular sense (APt-VS) interval associated with each of the atrial test pulses;
calculating an average of the APt-VS intervals; and
determining a midpoint of the ventricular sensing window as an average of the APt-VS intervals, wherein adjusting the default ventricular sensing window comprises adjusting the default ventricular sensing window to include the determined midpoint.

* * * * *